United States Patent [19]

Schuman et al.

[11] 4,024,143
[45] May 17, 1977

[54] SILYLATION OF 5-FLUORO-6-HYDROXY OR ALKOXY PYRIMIDINE

[75] Inventors: Paul D. Schuman, Hawthorne; Roy Anderson, Gainesville, both of Fla.

[73] Assignee: PCR, Inc., Gainesville, Fla.

[22] Filed: Mar. 11, 1976

[21] Appl. No.: 665,866

[52] U.S. Cl. .............................. 260/251 R; 536/23; 260/260

[51] Int. Cl.² ...................................... C07D 239/52

[58] Field of Search .................... 260/251 R; 536/23

[56] References Cited

UNITED STATES PATENTS 3,354,160  11/1967  Duschinsky et al. ................. 536/23
3,635,946   1/1972  Giller et al. ......................... 536/23

*Primary Examiner*—Dolph H. Torrence
*Attorney, Agent, or Firm*—Murray and Whisenhunt

[57] ABSTRACT

A process for producing bis-silyl derivatives of fluorinated pyrimidines is disclosed, wherein a 5-fluoro-6-hydroxy or alkoxy pyrimidine is reacted with a silane, such as triethylchlorosilane. The intermediate product produced by that reaction, which is obtained in high yield, may then be reacted with a further compound, which can be a blocked sugar halide or 2-chlorotetrahydrofuran, to produce a nucleoside of the pyrimidine. The nucleosides are useful as antibacterial and antiviral agents, and in the treatment of cancer.

13 Claims, No Drawings

SILYLATION OF 5-FLUORO-6-HYDROXY OR ALKOXY PYRIMIDINE

BACKGROUND OF THE INVENTION

This application relates to a process for producing bis-silyl derivatives of fluorinated pyrimidines, and to a process for producing nucleosides of pyrimidines, utilizing the bis-silyl derivative as an intermediate product.

U.S. Pat. No. 3,354,160 to Duschinsky et al, issued Nov. 21, 1967, discloses a process for preparing nucleosides of 5-fluorouracil and 5-fluorocytosine by reacting 5-fluorouracil or 5-fluorocytosine with hexa(lower alkyl)disilazane to form the corresponding bis-tri(lower alkyl) silyl-5-fluoropyrimidine intermediate compound, which can be subsequently condensed with an appropriate blocked sugar halide, and unblocked to form the desired nucleoside derivative.

Among the hexa(lower alkyl)disilazanes disclosed as suitable for the reaction of the aforesaid U.S. Pat. No. 3,354,160 is hexamethyldisilazane, sometimes known as HMDS.

The alkylation reaction of the aforesaid U.S. patent proceeds in high yields. However, one source of low process efficiency in the preparation of the desired nucleosides is in the preparation of the starting 5-fluorouracil or 5-fluorocytosine compound. Various methods of making these compounds are known to the prior art. Particularly preferred methods of making these compounds are disclosed in U.S. Pat. applications Nos. 186,444 and 271,489 filed Oct. 4, 1971 now U.S. Pat. No. 3,954,758 and July 13, 1972, respectively, the disclosures of which are hereby incorporated by reference. As disclosed in those applications, intermediate 5,6-dihydro compounds are formed which carry a 6-position hydroxy or alkoxy radical. These 5,6-dihydro compounds undergo an elimination reaction to obtain the desired 5-fluorouracil compound. Such a reaction involves a product loss of about 15%, on the conversion of uracil fluorohydrin to 5-fluorouracil.

U.S. Pat. No. 3,635,946, to Giller et al., issued Jan. 18, 1972 is directed to a process for preparing nucleosides of 5-substituted uracils by reacting 2-chlorofuranidine with bis-trimethylsilyl derivatives of the corresponding uracil. The reaction is conducted at a temperature of from −60 to +40° C, and the working examples (Examples 8 and 9) indicate that 50% and 65% yields, based on the theoretical yield, are obtained.

SUMMARY OF THE INVENTION

The present invention is directed to a process wherein nucleosides of 5-fluoropyrimidines can be produced in improved yields, as compared to the overall process using the nucleoside preparation step of U.S. Pat. No. 3,354,160 or U.S. Pat. No. 3,635,946. The present process involves reacting 5-fluoro-5,6-dihydro pyrimidines having a 6-hydroxy or alkoxy substituent with tri(lower alkyl) halosilane to form a bis-silylated product. The intermediate bis-silylated product can then be reacted with a blocked sugar halide, with a subsequent unblocking step, or with 2-chlorotetrahydrofuran, in order to produce the desired nucleoside product.

DETAILED DESCRIPTION OF THE INVENTION

Bis-silyl derivatives of fluorinated pyrimidines are produced by reacting at least one 5-fluoro pyrimidine of the formula

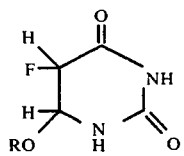

wherein R is hydrogen or lower alkyl of 1–6 carbon atoms, including lower fluoroalkyl with at least one silane of the formula

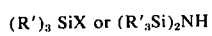

wherein each R' is lower alkyl of 1–6 carbon atoms and X is halogen, at a temperature of about room temperature to the boiling point of the reaction mixture, to produce a product of the formula

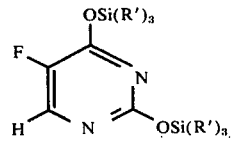

wherein R' is defined above. The lower alkoxy substituent on the pyrimidine ring may contain 1 or more halogen atoms, preferably fluorine atoms. Suitable starting pyrimidine compounds include 5-fluoro-6-hydroxy-5,6-dihydrouracil monohydrate, sometimes known as uracil fluorohydrin monohydrate, as well as 5-fluoro-6-methoxy-5,6-dihydrouracil, 5-fluoro-6-trifluoroethoxy-5,6-dihydrouracil, 5-fluoro-6-ethoxy-5,6-dihydrouracil, 5-fluoro-6-propoxy-5,6-dihydrouracil, 5-fluoro-6t-butoxy-5,6-dihydrouracil, and the like.

The silylating agent, whether only one or more silanes whether only one or more disilazanes, or mixtures thereof, will be used in at least stoichiometric amount, based on the starting pyrimidine compound.

The silane of the above formula may be trimethylchlorosilane, triethylchlorosilane, tripropylchlorosilane, tributylchlorosilane and the like. The use of tri(lower alkyl) halosilanes yields an essentially quantitative yield of the desired bis-silyl derivative. However, the reaction rate is slow. The use of hexa(lower alkyl)-disilazane alone can result in some product decomposition, thereby lowering the product yield.

Decomposition may be eliminated and increased yields achieved by use of mixtures of the two silylating agents. The tri(lower alkyl)halosilane in the mixture with a hexa(lower alkyl) disilazane should be in sufficient concentration to react with substantially all of the ammonia evolved in the silylation reaction. The disilazane may be hexamethyldisilazane, hexaethyldisilazane, hexabutyldisilazane, and the like.

Other tri(lower alkyl)halo silanes, such as the corresponding bromo compounds, can be used in full or partial replacement for the tri(lower alkyl)chlorosilanes. The reaction rate with trimethylchlorosilane as the sole silylating agent is so slow that the use of that silane alone is considered impractical, as little or no reaction occurs within practical time limits.

It has been found that the use of a mixture of tri(-lower alkyl)chlorosilane, including trimethylchlorosilane and hexa(lower alkyl)disilazane, suitably in a 50:50 mole ratio, but in more general terms from about 35 mole percent to about 50 mole percent to the disilazane, results in a reaction which proceeds without decomposition and at a reaction rate between that encountered with the silane alone and the disilazane alone. For this reason, the use of such a mixture, especially a mixture of trimethylchlorosilane and HMDS, is a particularly preferred embodiment of the present invention.

The increase in yield obtained by using the silylating agents of the present invention is particularly noticeable when the starting uracil compound contains water of hydration, such as, for instance, in the case of uracil fluorohydrin monohydrate. For the uracil compounds containing water of hydration, it appears that the disilazane silylating agent has a particularly noticeable problem with decomposition of the uracil compound during the course of the reaction. Thus, the highest improvements in yield achieved by the present invention will be noted when using a compound such as uracil fluorohydrin monohydrate as the starting compound.

Generally at least a stoichiometric amount of the silylating agent will be used, based on the starting pyrimidine compound. Molar equivalents of the silylating agent will react with the hydroxyl groups on the pyrimidine ring, and the silylating agent will also react with water of hydration and the reaction product of the elimination-dehydration reaction, which reaction product will be water or alcohol. Thus, for anhydrous compounds, at least 3 mols equivalents of the silylating agent will be required per mol of pyrimidine compound, and for the monohydrate starting compounds at least 4 mol equivalents of the silylating agent will be required per mol of starting pyrimidine compound. It will be appreciated that substantial excesses of silylating agent can be used, but no particular advantage will be realized.

When mixed silylating agents are used, it is quite important that the amount of tri(lower alkyl) halosilane used in the reaction mixture be sufficient to react with substantially all of the ammonia evolved in the silylation reaction of the hexa(lower alkyl)disilazane. In general, the amount of the halosilane compound will be at least a stoichiometric amount, based on the amount of water of hydration present in the pyrimidine compound, and the amount of alcohol or water formed as a reaction product by the dehydration/elimination reaction. As long as such minimum amount of halosilane is used, mixtures of the halosilane with the disilazane may be used with the advantages noted herein, as long as the total amount of silylating agent is an at least stoichiometric amount, based on starting pyrimidine compound.

The experimental results set forth in the working examples hereinbelow relate to reactions conducted at ambient pressures. However, these results suggest that the reaction rates could be increased if the boiling point of the reaction mixture was increased by using elevated pressures, such as, for instance, 30 psi. Preliminary results indicate that perhaps the preferred reaction conditions with the mixed silane/disilazane reagent would be under elevated pressures, of from about 1.1 atmospheres up to about 5 atmospheres, or even higher.

The reaction with the silylating agent appears to result in a dehydration-elimination reaction, to produce the desired bis-silyl derivative. It will be readily appreciated that the uracil compound can also be written in the tautomeric form, as follows:

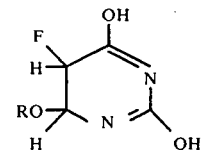

It would be theoretically possible, if the dehydration-elimination did not occur, for the tris-silyl derivative to be formed. However, under the reaction conditions utilized, only the bis-silyl derivative was obtained.

The chlorosilanes are much less reactive compounds than the disilazanes, such as HMDS, in reaction with the fluorohydrin, as well as with 5-fluorouracil itself. However, as indicated above, even though the reaction is slower, an essentially quantitative yield of bis-triethylsilyl-5-fluorouracil can be obtained by reacting the triethylchlorosilane with uracil fluorohydrin monohydrate. Substantially the same product will be produced from the 6-alkoxy pyrimidine derivative, which indicates that the reaction of the present invention is general for 6-OR-substituted-5,6-dihydro-5-fluorouracils.

If one were to follow the process of the aforesaid U.S. patent applications, Ser. Nos. 186,444 and 271,489, to prepare a compound suitable for a starting material in the silylation reaction taught by the aforesaid U.S. Pat. No. 3,354,160 or 3,635,946, 5-fluorouracil would be produced, and that compound could be reacted with the silane compound to produce the bis-silyl derivative of the uracil compound. In such a process, however, there would be about a 15% product loss in the conversion of the uracil fluorohydrin to 5-fluorouracil. A distinct advantage of the process of the present invention is in the elimination of this loss, as the applicants have unexpectedly found that uracil fluorohydrin can be directly silylated to produce the bis-silyl-5-fluorouracil compound. That compound can then be reacted with a blocked chlorosugar, or with 2-chlorotetrahydrofuran, to produce the desired nucleoside, generally in about 60% yield, based on the starting bissilyl-5-fluorouracil compound. The process of the present invention represents about an 18% overall improvement in yield, as compared to the process involving the conversion of the uracil fluorohydrin monohydrate to 5-fluorouracil, with subsequent silylation of that compound, and conversion into the desired nucleoside.

The reaction of the silylating agent with the 6-hydroxy or alkoxy substituted pyrimidine, as described above, proceeds at a temperature of about room temperature to the boiling point of the reaction mixture. Preferably, the reaction proceeds under reflux, as the reaction rate is reduced at lower temperatures.

After the desired intermediate bis-silyl pyrimidine derivative is obtained, the intermediate product may be reacted with 2-chlorotetrahydrofuran, or with a blocked sugar halide, at a temperature of about −60° C to about ambient temperatures, preferably about −50° C to 0° C, to produce the desired nucleoside product. The reaction of a bis-trimethylsilyl derivative of 5-fluorouracil with 2-chlorofuranidine is disclosed in U.S. Pat. No. 3,635,946, the disclosure of which is hereby incorporated by reference for the teaching of such process therein. The reaction of the bis-silyl derivative of 5-fluorouracil with blocked sugar halides is described in U.S. Pat. No. 3,354,160, the disclosure of which is hereby incorporated by reference for the teaching of such process therein.

The reaction with the silylating agent may be carried out either in an inert organic solvent, such as dioxane, toluene, or the like, or may be conducted in the absence of any solvent. The condensation of the bis-silyl pyrimidine intermediates with a blocked sugar halide may be conducted in the absence of a solvent or with an inert solvent medium, such as a hydrocarbon medium, such as toluene, benzene, etc., or in ethers, such as dioxane, etc. When reacting chlorotetrahydrofuran with the bis-silyl pyrimidine derivative, it is preferred to use an anhydrous organic solvent, such as toluene or tetrahydrofuran.

The resulting nucleosides prepared from the intermediate products produced by the process of the present invention are pharmaceutically useful compounds, and in particular may be used as antibacterial and antiviral agents. Certain of the compounds are useful in treating sarcoma 180 and Walker carcinosarcoma in mice.

EXAMPLES OF THE INVENTION

EXAMPLE 1

Preparation of bis-trimethylsilyl-5-fluoro-uracil 5-fluoro-6-hydroxy-5,6-dihydrouracil monohydrate, 8.3 g, was boiled under reflux with hexamethyldisilazane (47 ml) and chlorotrimethylsilane (0.5 ml) for 18 hours. Distillation of the resulting product under reduced pressure (0.35 mm Hg) produced bis-trimethylsilyl-5-fluorouracil, 9.5 g (60% yield, based on theory).

EXAMPLE 2

Preparation of bis-trimethylsilyl-5-fluorouracil 5-fluoro-6-(2,2,2-trifluoroethoxy)-5,6-dihydrouracil, 5.76 g, was boiled under reflux with hexamethylsilazane, 24.2 g, for 16 hours. Distillation of the resulting product gave bis-trimethylsilyl-5-fluorouracil 5.6 g (67% yield, based on theory).

EXAMPLE 3

Preparation of bis-trimethylsilyl-5-fluorouracil

Anhydrous 5-fluoro-6-hydroxy-5,6-dihydrouracil, 29.6 g, was stirred under reflux with hexamethyldisilazane, 113 g, for 20 hours. A clear solution was obtained. Distillation at 1.5 mmHg gave 43.6 g (80% yield, based on theory) of bis-trimethylsilyl-5-fluorouracil, boiling at 82°–85° C at 1.5 mm.

EXAMPLE 4

Preparation of bis-triethylsilyl-5-fluorouracil 5-fluoro-6-hydroxy-5,6-dihydrouracil monohydrate, 4.15 g, was boiled under reflux with chlorotriethylsilane, 50 ml. Distillation of the resulting product gave a quantitative recovery of bis-triethylsilyl-5-fluorouracil.

EXAMPLE 5

Example 1 was repeated, but the chlorotriethylsilane was replaced with an equivalent amount of bromotrimethylsilane, producing an essentially quantitative yield of bis-trimethylsilyl-5-fluorouracil.

EXAMPLE 6

Preparation of bis-trimethylsilyl-5-fluorouracil 5-fluoro-6-hydroxy-5,6-dihydrouracil monohydrate, 33.2 g, was heated under a reflux with a mixture of HMDS, 72.6 g, and chlorotrimethylsilane, 48.9 g, for 51 hours. The reaction mixture was filtered and the filtrate distilled to give 45.0 g (82% yield, based on theory) of bis-trimethylsilyl-5-fluorouracil, boiling at 65°–68° C at 0.35 mm. An undetermined amount of 5-fluorouracil was detected in the solid filtrate by thin layer chromotography.

EXAMPLE 7

Preparation of 1-(tetrahydro-2-furanyl)-5-fluorouracil

A solution of 2-chlorotetrahydrofuran, 17 g, in tetrahydrofuran, 11.5 g, cooled below −40° C, was slowly added to a solution of bis-trimethylsilyl-5-fluorouracil, 19.3 g, in tetrahydrofuran, 20 ml, maintained at −45° C. The resulting product was slowly added to a solution of ammonium hydroxide, 8 ml, in methanol, 120 ml, maintained at −45° C. The resulting product was filtered, and the filtrate evaporated to dryness. The residue was extracted with chloroform, and the extract evaporated to dryness to yield 7.1 g of product. This product was recrystallized from isopropanol to yield a white solid, identified by comparison of I.R. spectra as 1-(tetrahydro-2-furanyl)-5-fluorouracil.

We claim:

1. A process for producing bis-silyl derivatives of fluorinated pyrimidines, said process comprising reacting a 5-fluoropyrimidine of the formula

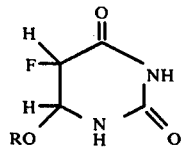

or the monohydrate thereof, wherein R is hydrogen or lower alkyl, including lower fluoroalkyl, with at least a stoichiometric amount of silylating agent which is a. silane of the formula

wherein each R' is lower alkyl and X is halogen, and/or b. disilazane of the formula

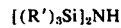

wherein R' is lower alkyl,
at a temperature of about room temperature to the boiling point of the reaction mixture, to produce a product of the formula

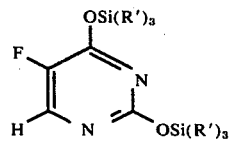

wherein R' is defined above.
2. Process of claim 1 wherein, X is chlorine
3. Process of claim 1 wherein, R is hydrogen.
4. Process of claim 1 wherein, R is lower alkyl.

5. Process of claim 1, wherein said silylating agent is a mixture of said silane and at least about 35 to about 50 mol % of disilazane.

6. Process of claim 5, wherein said fluoropyrimidine contains water of hydration.

7. Process of claim 1, wherein said disilazane is hexamethyldisilazane.

8. Process of claim 1, wherein said reaction is conducted under reflux conditions.

9. Process of claim 1, wherein the product is bis-trimethylsilyl-5-fluorouracil.

10. Process of claim 1, wherein the product is bis-triethylsilyl-5-fluorouracil.

11. Process of claim 1, wherein the starting pyrimidine compound is an anhydrous compound, and at least 3 mol equivalents of silylating agent are used, wherein at least one mole equivalent of the silylating agent is said silane.

12. Process of claim 1, wherein the starting pyrimidine compound is a monohydrate, and at least 4 mol equivalents of the silylating agent are used, wherein at least 2 mols of said silane are used.

13. Process of claim 1, wherein at least part of said silylating agent is said silane, and the amount of said silane is at least a stoichiometric amount, based on the —OH, RO— groups and the water of hydration present in said pyrimidine compound.

* * * * *